(12) United States Patent
Van De Weghe et al.

(10) Patent No.: US 9,480,466 B2
(45) Date of Patent: Nov. 1, 2016

(54) SURGICAL DEVICE AND LINKAGE SYSTEM FOR SAME

(71) Applicant: CareFusion 2200, Inc., San Diego, CA (US)

(72) Inventors: Andrew P. Van De Weghe, Grayslake, IL (US); Louis P. Mingione, Mundelein, IL (US); David A. Schechter, Boulder, CO (US); David Scott Hazlitt, Boulder, CO (US)

(73) Assignee: CareFusion 2200, Inc., San Diego, CA (US)

( * ) Notice: Subject to any disclaimer, the term of this patent is extended or adjusted under 35 U.S.C. 154(b) by 222 days.

(21) Appl. No.: 14/292,210

(22) Filed: May 30, 2014

(65) Prior Publication Data

US 2015/0342583 A1    Dec. 3, 2015

(51) Int. Cl.
*A61B 17/00* (2006.01)
*A61B 17/29* (2006.01)
*A61B 17/28* (2006.01)

(52) U.S. Cl.
CPC ......... *A61B 17/00234* (2013.01); *A61B 17/28* (2013.01); *A61B 17/29* (2013.01); *A61B 2017/0046* (2013.01); *A61B 2017/00424* (2013.01); *A61B 2017/00464* (2013.01); *A61B 2017/292* (2013.01)

(58) Field of Classification Search
None
See application file for complete search history.

(56) References Cited

U.S. PATENT DOCUMENTS

| 5,489,290 | A | 2/1996 | Furnish |
| 5,498,256 | A | 3/1996 | Furnish |
| 5,507,297 | A | 4/1996 | Slater et al. |
| 5,665,105 | A | 9/1997 | Furnish et al. |
| 5,827,323 | A | 10/1998 | Klieman et al. |
| 5,922,007 | A | 7/1999 | Hoogeboom et al. |
| 5,947,996 | A | 9/1999 | Logeman |
| 6,000,138 | A | 12/1999 | Bornancini |
| 6,077,290 | A | 6/2000 | Marini |
| 7,846,177 | B2 | 12/2010 | Carpenter et al. |
| 8,512,315 | B2 | 8/2013 | Leonard et al. |
| 2007/0299469 | A1 | 12/2007 | Carpenter et al. |
| 2008/0021278 | A1 | 1/2008 | Leonard et al. |

(Continued)

FOREIGN PATENT DOCUMENTS

| EP | 1348381 A2 | 1/2003 |
| WO | WO 94/25710 | 12/1994 |

(Continued)

OTHER PUBLICATIONS

*Modular Laproscopic-Instruments*, Pajunk.

(Continued)

*Primary Examiner* — Lynsey Crandall
*Assistant Examiner* — Qingjun Kong
(74) *Attorney, Agent, or Firm* — Brinks Gilson & Lione

(57) ABSTRACT

A laparoscopic surgical device is provided, including a removable tool-comprising shaft having an outer shaft and an inner actuation rod that may be removably or permanently connected together. A handle of the device includes a two-button mechanism for engaging and releasing the removable tool-comprising shaft. The two-button mechanism is configured to engage overlapping corresponding apertures of the outer shaft and the inner rod that extends through the outer shaft, and the handle may include a variety of configurations that can readily interchangeably be used with different tool bodies.

20 Claims, 13 Drawing Sheets

(56) References Cited

U.S. PATENT DOCUMENTS

2008/0306342 A1* 12/2008 Leonard ............. A61B 17/2909
  600/131
2010/0191225 A1   7/2010 Leonard
2011/0112517 A1*  5/2011 Peine ................. A61B 17/29
  606/1
2011/0306952 A1  12/2011 Chen et al.

FOREIGN PATENT DOCUMENTS

WO   WO 2008 002574 A2   1/2008
WO   WO 2008/154289     12/2009

OTHER PUBLICATIONS

*Diamond-Line Laparoscopic Surgical Instruments.*
*The Economic Scissor System with Disposable Inserts*, Panjunk GmbH.
*Diamond-Line Laparoscopic Surgical Instruments*, Snowden-Pencer® MIS Products.
*Think blue for ergonomics, versatility and durability*, Snowden-Pencer® in-line and pistol-grip laparoscopic instruments.
*Snowden-Pencer® next generation reusable ring-handled laparoscopic instruments*, CareFusion.
International Search Report and Written Opinion for International Application No. PCTUS/2015/028146, mailed Jun. 28, 2015.

* cited by examiner

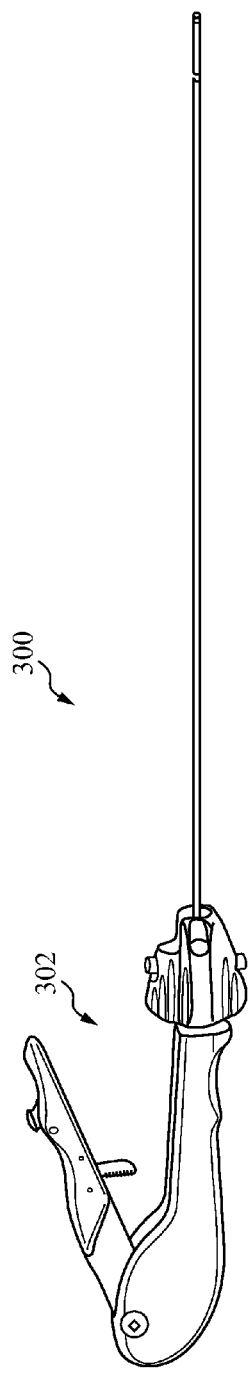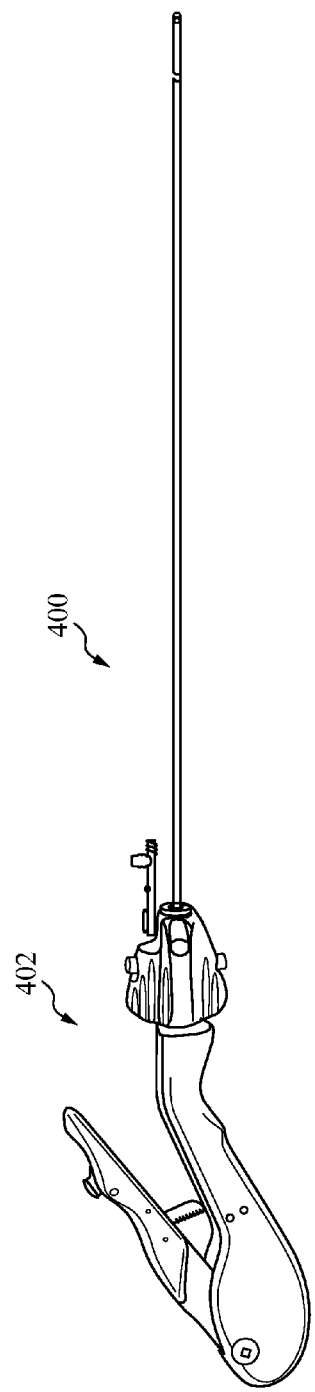
FIG. 5A
FIG. 5B

SURGICAL DEVICE AND LINKAGE SYSTEM FOR SAME

FIELD OF THE INVENTION

The present invention relates generally to medical devices, and more particularly to a laparoscopic surgical device configured with a removable tool end assembly, and with a linkage system allowing for interchange of different actuator handles.

BACKGROUND

As depicted in FIG. 1, a typical monopolar electrosurgical laparoscopic tool device 100 generally has five main components: a handle 102, an outer shaft 104 extending longitudinally from the handle, an actuation rod 106 extending through the outer shaft, an electrode 108 in electroconductive contact with the actuation rod, and an actuatable end effector 110, disposed at the distal end of the device. The handle 102 illustrated is a "ring handle", which has a stationary finger portion 112 attached to the outer shaft 104 and an actuatable thumb portion 114 attached to the actuation rod 106. Actuation of the thumb portion 114 by pivoting relative to the finger portion 112 moves the actuation rod 106 axially within the outer shaft 104 to operate the end effector 110. Although many different variations of each of the above components have been introduced into the art, there exists a need for designs that provide efficiency in manufacturing, and that provide surgeons and other users with ergonomic features to enhance safety and ease of use. In particular, there is a need for a handle design that includes an easy-to-use locking feature that provides for secure attachment and convenient detachment of a tool end assembly.

BRIEF SUMMARY

Embodiments of the present invention are configured to address the needs in the art for ergonomic and economically-efficient designs that present advantages in manufacture and use while helping medical facilities and patients to control expense. Preferred embodiments of the present invention may be configured such that they may be cleaned, sterilized, and reused, or they may be disposable. The most preferred embodiments of the present invention include a tool end retention mechanism that is biased so as to engage a one-piece or two-piece tool end assembly, which can be released using a two-button component of the retention mechanism, certain embodiments of which are shown in U.S. Pat. App. Publ. No. 2011/0306952 to Chen et al., which is incorporated herein by reference in its entirety. This retention mechanism provides a secure engagement of an outer shaft and an inner actuation rod of a tool end, as well as a handle that may be reusable. In certain embodiments, reusable tool end/tool tip assemblies may also be used. While embodiments of the present invention discussed herein are directed to aspects of a handle for a laparoscopic surgical device, those of skill in the art will appreciate that handle embodiments of the present invention may be used with a variety of shaft configurations and end effectors (e.g., needle holders, clamps, scissors, dissectors, graspers), and that such uses may be practiced within the scope of the present invention.

In one aspect, embodiments of a surgical device handle may include a tool body that includes an inner actuation rod reciprocally disposed through a longitudinal lumen of an outer shaft, where the distal ends of the rod and shaft may be permanently attached or may be removably attached with each other and/or with a tool tip. In another aspect, each handle of an in-line configuration and/or an off-set pistol grip configuration includes a linkage member that provides for engagement with an actuation rod of a tool body that may interchangeably be used between those handle configurations and a standard pistol grip handle.

BRIEF DESCRIPTION OF THE DRAWINGS

FIG. 5A shows a laparoscopic surgical device embodiment with an in-line handle;

FIG. 5B shows a laparoscopic surgical device embodiment with an off-set pistol-grip handle;

DETAILED DESCRIPTION

Figure 1:
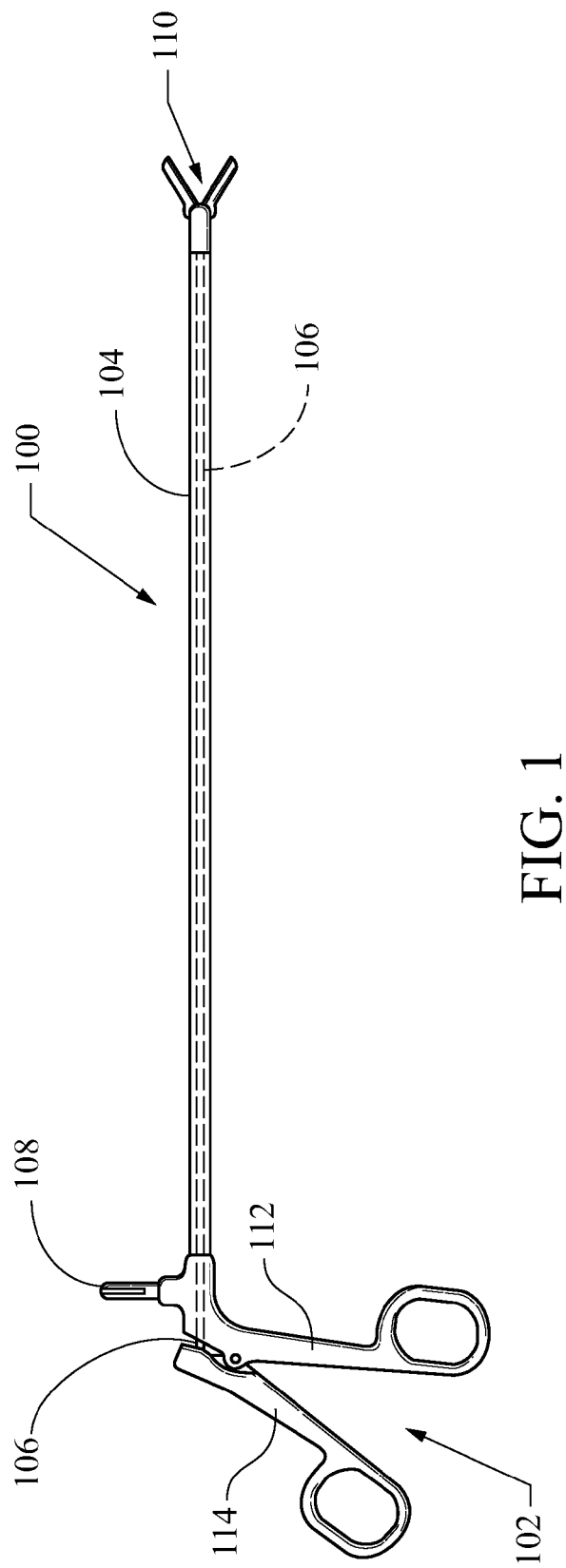
FIG. 1 shows a prior art laparoscopic tool device.
Figure 2:
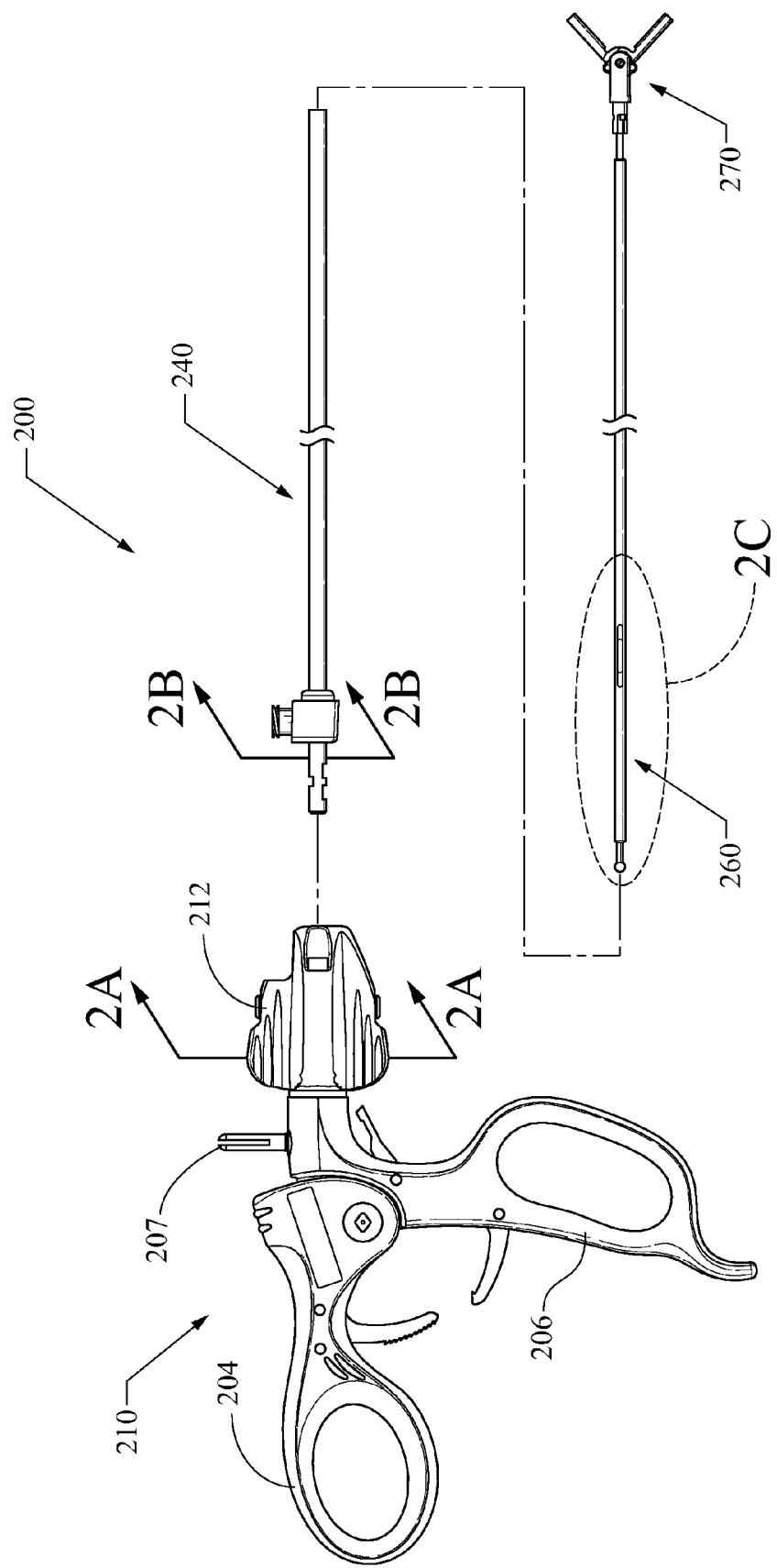
FIG. 2 illustrates a disassembled view of first embodiment of a laparoscopic device including a pistol-grip handle embodiment.

The exterior of a first embodiment of a laparoscopic surgical device 200 is illustrated with reference to FIGS. 2-2C. As shown in FIG. 2, which is a disassembled view of a "three-piece embodiment," the handle 210 includes a thumb ring member 204 (commonly referred to as a "thumb bow") pivotably attached at a pivot pin 208 to a finger ring member 206 (commonly referred to as a "finger bow"). The handle members 204, 206 preferably are biased away from each other by, for example, a torsion spring or leaf spring. The thumb and finger ring members 204, 206 preferably are constructed of a resin material but may alternatively be constructed of plastic or other materials known in the art to be suitable for multiple sterilizations in an autoclave. A single-use embodiment may be constructed of materials known in the art, but not necessarily configured for multiple sterilizations. The device 200 may be configured as a monopolar or bipolar instrument configured for cutting and coagulation/electrocautery, including a Bovie post 207 or other electrode connection. A knob 212, configured to rotate about its longitudinal axis in an indexed or smooth-rotating manner (various constructions for both of which are well-known in the art), may be included at the distal end of the handle 210.

A tool end body including an elongate tubular outer shaft 240 extends distally from the finger ring member 206. An actuation rod 260 extends distally from the thumb ring member 204 through a longitudinal lumen of the shaft 240 and includes a tool tip 270 at its distal end. At the distal end of the device 200, an end effector 264 is operably connected both to the shaft 240 and the actuation rod 260. The actuation rod connection to the outer shaft 240 may be permanent, or it may be removable (e.g., with a bayonet, threaded, snap-fit, or other connection). The shaft 240 may be constructed of metallic or polymeric materials, and preferably has an electroinsulative coating when the device 200 is configured as an electrosurgical instrument with a length that will most often be rigid, semi-rigid, or have very limited flexibility along its longitudinal axis. The shaft 240 preferably is configured for use with laparoscopy trocars for abdominal or other laparoscopic/minimally invasive surgical techniques (e.g., standard embodiments may have an outer diameter of about 5 mm to about 10 mm). All components of preferred embodiments will be configured to maintain fluid seal conditions desirable for use during a procedure on an insufflated patient. The handle 210 may include one or more ratchet mechanisms configured to assist a user in positioning and operating the device 200. Detailed depictions of handle construction as well as examples of ratchet and other retention/manipulation mechanisms that may be used within the scope of the present invention include those described in U.S. Pat. App. Publ. No. 2007/0299469, to Carpenter et al., which is incorporated herein by reference.

Figure 2A:
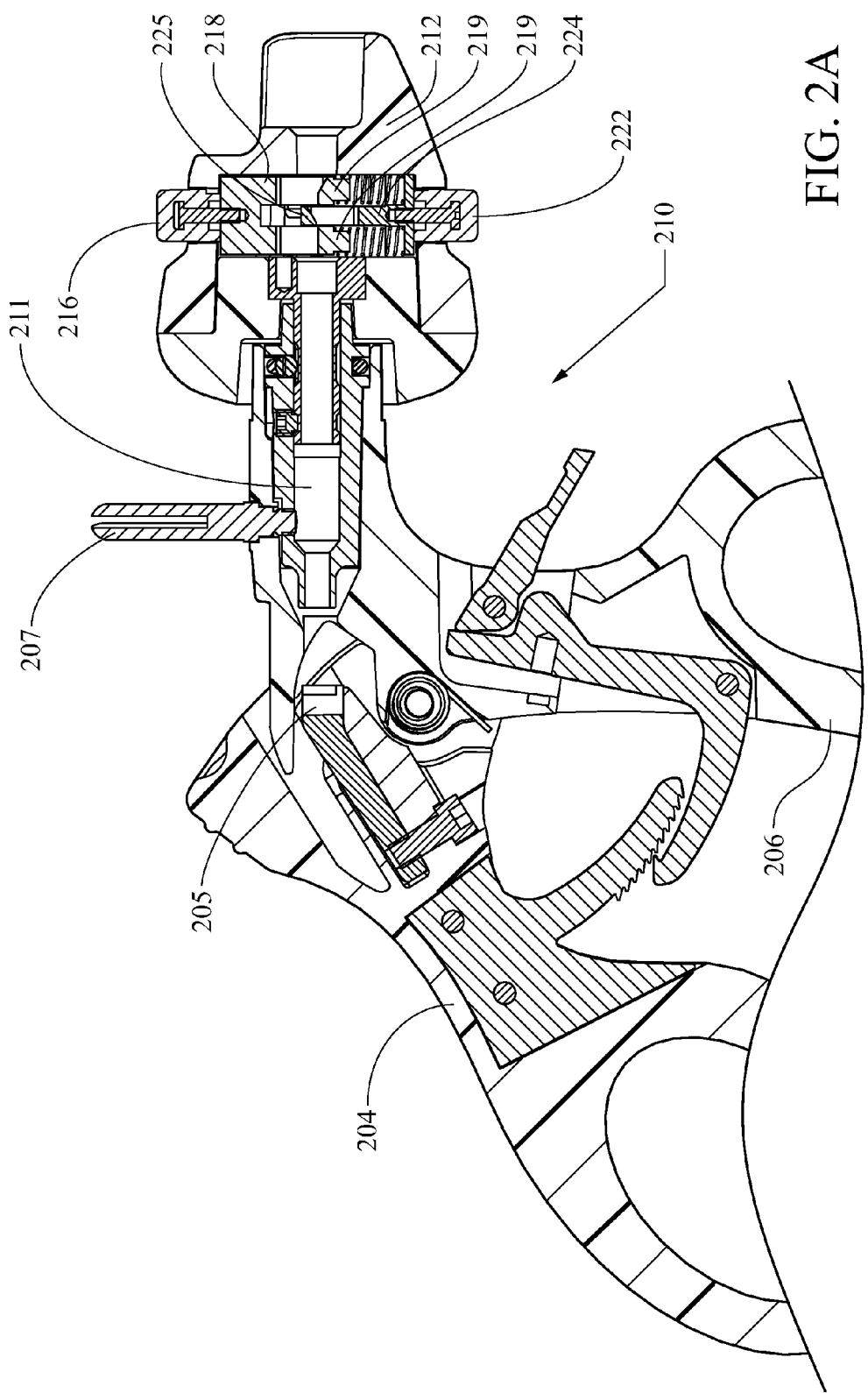
FIG. 2A shows a longitudinal section view, taken along line 2A-2A of FIG. 2, of the tool body retention mechanism of the first handle embodiment.

FIG. 2A is a partial longitudinal section view of the handle 210 along line 2A-2A, showing the handle portion of an engagement mechanism for releasably connecting the tool body shaft 240 to the handle 210. A central channel 211 extends through the knob 212 and the upper portion of the finger bow handle member 206. This channel 211 is configured to receive the proximal ends of the tool body outer shaft 240 and inner actuation rod 260. The thumb ring handle member 204 includes an opening 205 configured as a ball-cage that is configured to capture a proximal-end ball 262 of the actuation rod 260.

The knob 212 substantially houses the shaft-engagement and rod-engagement portions of the engagement mechanism (the ball-cage 205 of the thumb bow 204 not being considered part of the engagement mechanism for purposes of the present description, although it serves an important function in retaining/actuating the inner rod 260). The knob includes two opposing, depressible buttons 216, 222. As shown in FIG. 2A, the first button 216 is attached to and disposed opposite a two-toothed retaining member 218, which includes teeth 219 that are biased up toward the first button 216 into the channel 211. The second button 222 is attached to and disposed opposite a one-toothed retaining member 224, which includes a tooth 225 that is biased down toward the second button 222 into the channel 211. As shown, the retaining members and their teeth (which collectively may be referred to as "shutters") are permanently attached to the handle 210 and in direct mechanical communication with their respective/corresponding buttons. Actuation of the retaining members is described below with reference to FIGS. 3A-3B. The bias for each of the retaining members is shown as being provided by coil springs, but other biasing means may be used, as known in the art.

Figure 2B:
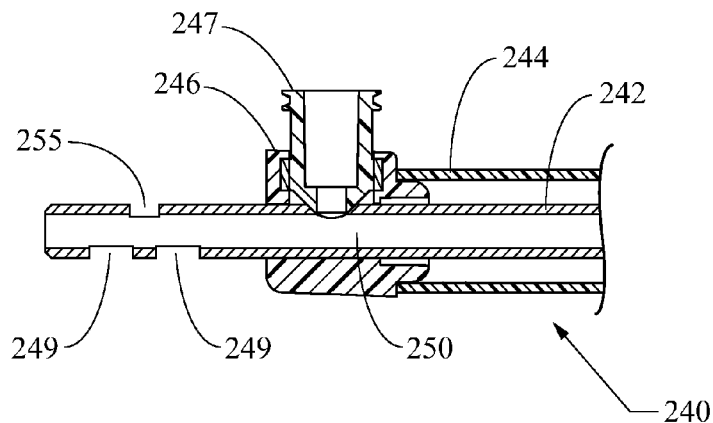
FIG. 2B is a longitudinal sectional view of a proximal portion of the tool body outer shaft assembly taken along line 2B-2B of FIG. 2.

FIG. 2B shows a longitudinal section view (taken along line 2B-2B of FIG. 2) of the proximal portion of the tool end body shaft assembly 240. In this embodiment, an inner portion 242 of the shaft 240 is metal, and an outer covering portion 244 includes an electroinsulative polymer. In the embodiment shown, which is a "larger outer diameter" embodiment, the outer covering 244 is separated from the inner portion 242 of the shaft 240, but—in certain "smaller outer diameter" embodiments, the outer covering 244 may be directly in contact with and/or be constructed as an overlay of the inner shaft portion 242. A nose portion 246, configured to be received in a complementarily shaped cavity of the knob 212 is mounted near the proximal shaft end. The nose portion 246 includes a flush port 247 that provides fluid communication with a longitudinal lumen 250 extending through the length of the shaft 240. A proximal endmost portion of the shaft 240, which is configured to be received into the handle channel 211, includes at least first and second apertures that are at least partially opposed to each other. In the embodiment shown in FIGS. 2-3C, the first aperture is embodied as a pair of apertures 249 configured to align with and receive the first retaining member teeth 219. The second aperture is embodied as an aperture 255 that is disposed opposite the first aperture and is configured to align with and receive the second retaining member tooth 225.

Figure 2C:
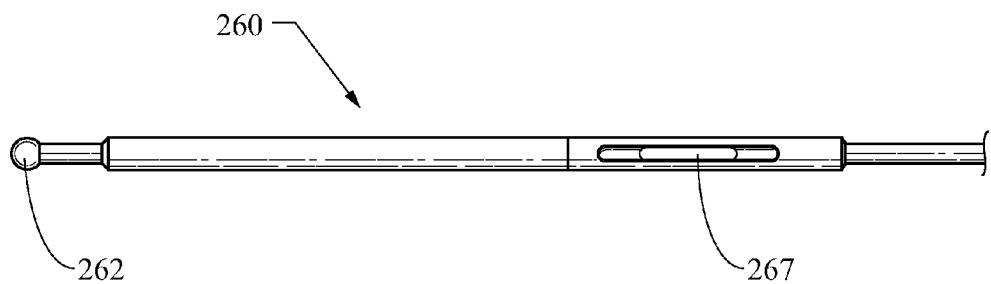
FIG. 2C shows a detail view of a proximal end portion of the actuation rod of the device of FIG. 2.

FIG. 2C shows an external top-down view of the proximal portion of the actuation rod 260. A ball 262 or other flared structure is disposed at its proximal end, configured for capture by the upper end of the thumb-ring handle member 204. The ball 262 may include a larger outer diameter than a majority length of the rod 260 and most preferably includes a larger outer diameter than a rod portion immediately distally adjacent the ball. The inner rod 260 is configured to be slidably disposed through the shaft lumen 250. As shown, a proximal rod length may include a larger outer diameter than a majority length of the rod 260 that will facilitate flushing of the shaft lumen 250 with the rod not being removed therefrom while providing a desirable proximal seal therebetween. Pivoting actuation of the thumb bow 204 relative to the finger bow 206 will longitudinally reciprocate the inner rod 260 relative to the shaft 240. At its distal end the rod 260 includes a tool assembly 270 that is configured to be attached to the outer shaft 240. This attachment may be removable, as is described below with reference to FIG. 3C, or it may be permanent such that the shaft 240 and rod 260 may be attached/removed from the handle 210 as a single unit. Embodiments where the rod and shaft are permanently connected may be configured to have the distal rod/shaft/tool assembly disposable after a single use or configured to be cleaned and/or sterilized. Many different tool tip assemblies 270 are known in the prior art for use/actuation with a reciprocating inner rod and an outer shaft that is relatively fixed. Tool tips may include clamps, graspers, cutting scissors, or other actuatable tool tips currently known or later-developed, while being practiced within the scope of the present invention. The inner rod 260 may be constructed as a single piece, or in multiple pieces, including that one or more portions (in addition to the proximal ball 262 may have a larger outer diameter than a majority length of the rod).

A proximal region of the rod 260 includes an elongate inner rod groove or aperture 267. The inner rod aperture 267 is shown as generally obround, but may have varied internal geometry including that it may be embodied as a pair of opposing grooves that do not go all the way through the rod (not shown, but easily able to be understood by those of skill in the art as including a longitudinal wall between the opposed faces of the aperture 267). It is configured to receive the ends of the first and/or second retaining member teeth 219, 225. When the teeth 219, 225 are engaged with the inner rod aperture 267, they will allow it to reciprocate longitudinally, but will generally prevent the rod 260 from rotating about its longitudinal axis. As such, when the teeth 219, 225 are engaged through the outer shaft apertures 249, 255 into the inner rod aperture 267, they (the teeth) will: (i) generally maintain the outer shaft 240 in a fixed longitudinal and rotational position relative to the handle 210; and (ii) generally maintain the inner rod 260 in a fixed rotational position relative to the outer shaft 240 and handle 210 while permitting it to reciprocate longitudinally relative to the handle 210 and outer shaft 240 upon pivoting actuation of the thumb bow 204 relative to the finger bow 206. This structure and its related functionality are described below with reference to a method of assembling the device 200.

Figure 3A:
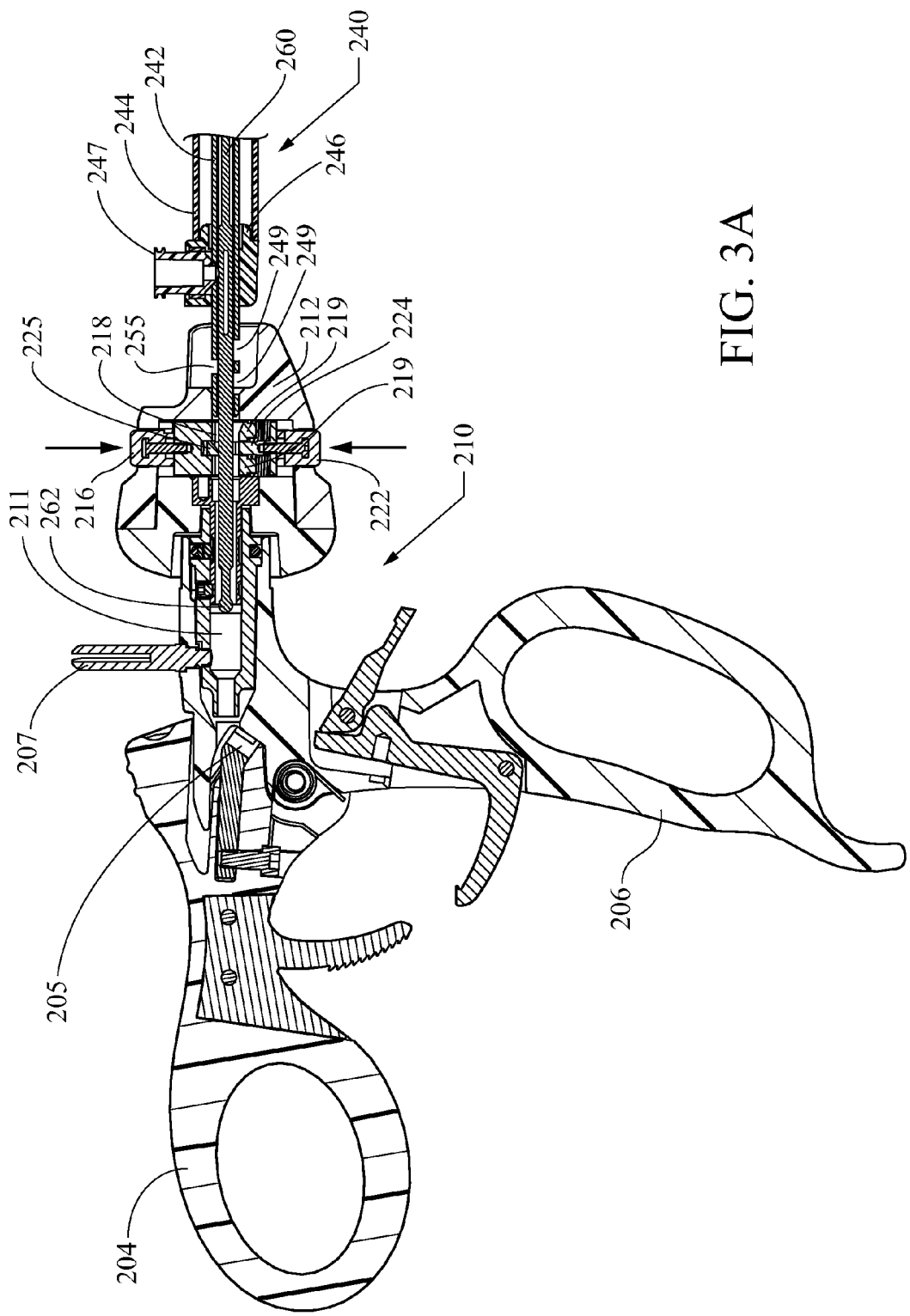
FIGS. 3A-3B show a section view as in FIG. 2A, illustrating a method of assembly.
Figure 3B:
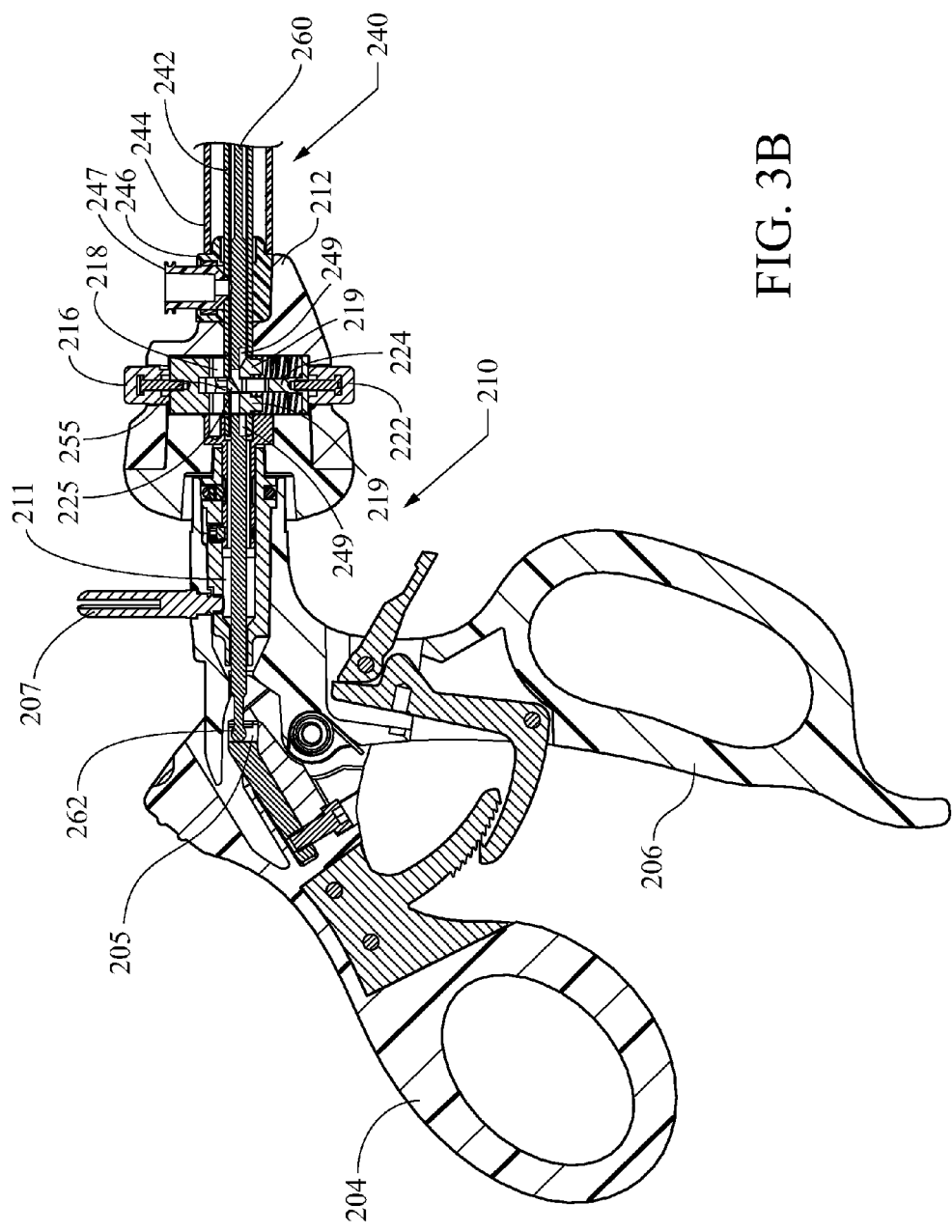

In most embodiments, the thumb bow 204 will be rotatable relative to the finger bow 206 in only a single plane. However, handle constructions are known in the art, where out-of-plane rotation maybe used. Preferred embodiments of the device 200 will include insulative material over all handle and other proximal-region surfaces that are likely to conduct current when the device is configured as an electrosurgical device and attached to an electrosurgical power supply. As shown in FIG. 3B, discussed below, in embodiments where a nose portion is used, it is permanently fixed to the outer shaft and will prevent the outer shaft from rotating relative to the engagement mechanism (whether that engagement mechanism is disposed in an indexing knob, as shown, or disposed in a fixed portion of the handle assembly 210).

A method of assembling the device 200 of FIGS. 2-2C is described with reference to FIGS. 3A-3C. In FIG. 3A, the thumb bow 204 is over-rotated up and away from the finger bow 206. This orientation exposes a top end opening of the ball-cage 205 in line with the proximal end of the longitudinal handle channel 211. The inner rod 260 is disposed through the shaft lumen 250 and longitudinally directed into the handle channel 211. The first and second buttons 216, 222 are depressed in toward the central longitudinal axis of the engagement mechanism in the indexing knob 212. This actuation of the first button 216 pushes the teeth 219 of the two-toothed retaining member 218 down and out of the handle channel 211. Likewise, this actuation of the second button 222 pushes the tooth 225 of the second retaining member 224 up and out of the handle channel 211.

With the retaining teeth 219, 225 held out of the way, the handle channel 211 allows the inner rod 260 and outer shaft 240 to be advanced proximally thereinto until the proximal ball 262 of the rod enters and is captured by the ball-cage 205. As shown in FIG. 3A, one or more of the teeth 219, 225 may have an angled, cambered, or rounded distal surface such that the rod 260 and/or shaft 240 can more readily approach, dislodge, and pass the teeth, even if the buttons 216, 222 are not initially fully depressed. The thumb bow 204 can be released and directed/pivoted down toward the finger bow 206, fully capturing the ball 262 in the ball-cage 205, which has a key-hole cross section such that a broader proximal portion engages the ball 262 while a narrower distal portion prevents the ball from being released distally when the thumb bow 204 is rotated down as shown in FIG. 3B. The ball-cage 205 preferably will not interfere with actuation of the handle members nor of rotation of the inner rod 260 about its longitudinal axis. The elongate inner rod aperture 267 is visible in FIG. 3A, with the rod 260 and outer shaft 240 being shown about 90 degrees out of the rotational position that will allow the retaining teeth 219, 225 to engage that inner rod aperture 267 through the outer shaft apertures 249, 255.

FIG. 3B shows the tool body assembly including the outer shaft 240 and inner rod 260 as being fully advanced proximally. The shaft 240 and rod 260 have been rotated and the buttons 216, 222 have been released so that: (i) the shaft apertures 249, 255 are aligned with the inner rod aperture 267; (ii) the retaining teeth 219, 225 are extended into their respective biased positions to engage the inner rod aperture 267 through the outer shaft apertures 249, 255; and (iii) the nose portion 246 is aligned and engaged with the indexing knob 212. As shown in this engaged configuration/position, the inner rod 260 will reciprocate longitudinally relative to the outer shaft 240 and finger bow 206, which are longitudinally fixed relative to each other. In embodiments where the indexing knob 212 is rotatable, the knob 212, outer shaft 240, and inner rod 260 can rotate relative to the handle 210 about their mutual longitudinal axis.

Figure 3C:
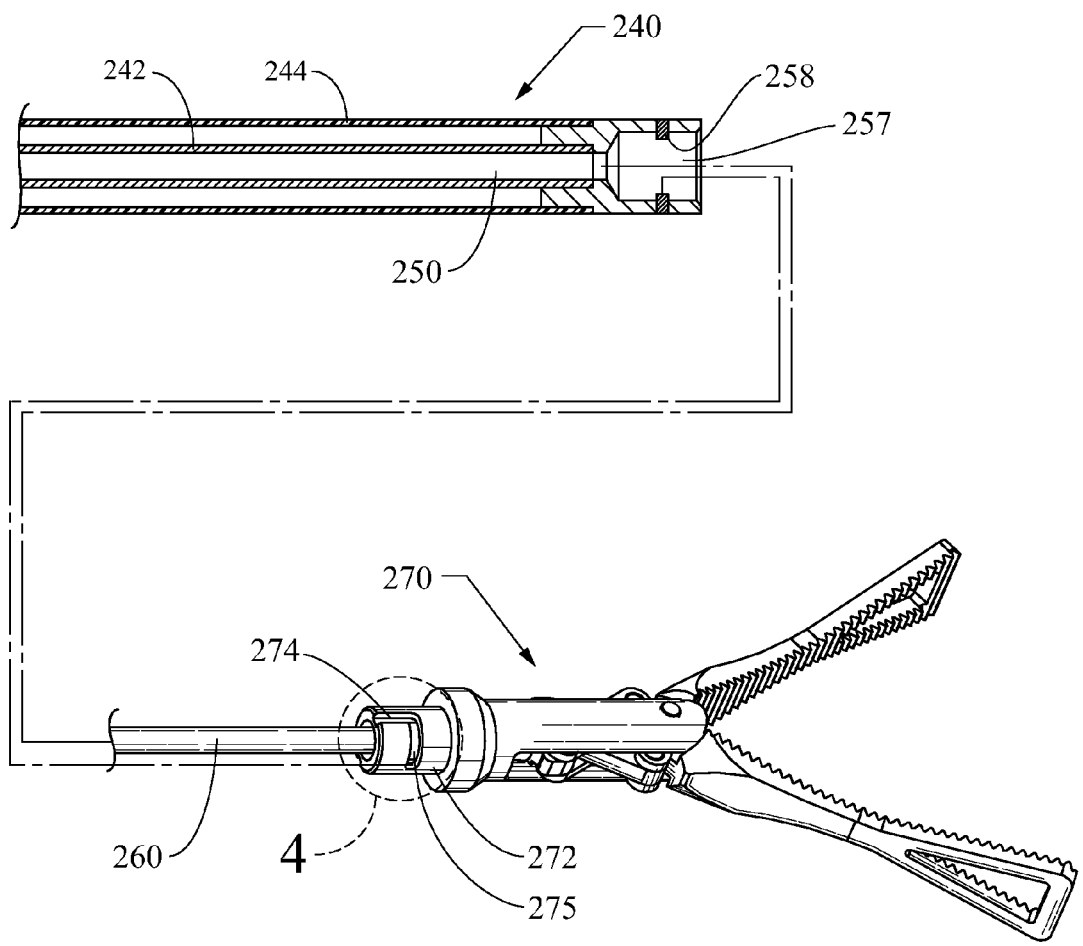
FIG. 3C shows a distal end connection embodiment between the actuation rod and tool end shaft body.
Figure 4:
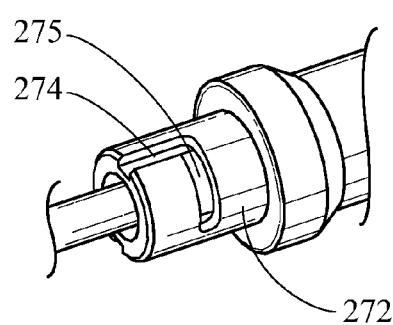
FIG. 4 shows a detail perspective view of the distal end connection embodiment from FIG. 3C.

FIG. 3C shows one connection construction for embodiments of the device 200 wherein the inner rod 260 is removable from the outer shaft 240 rather than being permanently distally attached thereto. The tool tip 270 is shown as a grasper assembly, but may be constructed as cutting scissors, biopsy forceps, or any number of other laparoscopy-type tool tips. The proximal base 272 of the tool tip body is generally cylindrical and includes a bayonet groove having a longitudinal groove portion 274 and a radial groove portion 275. The inner rod 260 is axially movable relative to the base 272. FIG. 3C also shows the distal end of the outer shaft 240, which includes a distal opening 257 configured to snugly receive the tip base 272. A groove-engaging pin 258 extends radially into the opening 257. FIG. 4 shows a perspective detail view of FIG. 3C.

When the actuation rod 260 is directed into the shaft lumen 250, the groove engaging pin 258 can be guided to the distal end of the longitudinal bayonet groove portion 274, then the tool tip can be rotated to engage the pin 258 to the end of the radial groove portion 275. The bayonet mechanism including the pin and groove preferably is constructed such that when the pin 258 is fully engaged at the end of the groove 275, the rotational position of the inner rod 260 aligns its proximal aperture 267 with the outer shaft apertures 249, 255. It should be appreciated that one, two or more bayonet pins and grooves may be used in various embodiments. In other embodiments, a threaded connection including a Luer-like connection requiring only a fractional turn for engagement (e.g., quarter-turn) or traditional multi-twist threading, snap-fit, reverse-bayonet, and/or other connection structures may be used to effect a connection between the distal ends of the shaft 240 and rod 260, without departing from the scope of the present invention. Whether or not the rod and shaft are engaged with a handle, it is preferable that a distal connection of the outer shaft is configured to engage the distal regions of the inner rod and the outer shaft when the inner shaft aperture is rotationally aligned with at least one of the outer rod apertures.

In view of the ease of use and other advantages for the tool body and engagement/release system described above, it would be further advantageous to provide for using the same or a similar system with other handle configurations. Specifically, as will be appreciated by those of skill in the art of laparoscopic surgical procedures, different handle configurations may be useful for different specific procedures (e.g., bariatric procedures) while using the same tool body and/or tool tip configurations for grasping, cutting, clamping, or otherwise manipulating tissue and surgical appliances (e.g., sutures, staples, needles, etc.). One example of known handle configurations is shown in FIG. 5A as an in-line handle 302 of a laparoscopic surgical device 300 including a tool body attached to the handle 302 with a two-button or other connection device (e.g., as shown and described above).

Another example of known handle configurations is shown in FIG. 5B as an off-set pistol-grip handle 402 of a laparoscopic surgical device 400 including a tool body attached to the handle 402 with a two-button or other connection device (e.g., as shown and described above), where the main gripping portion of the handle body is offset from the primary device longitudinal axis and is approximately intermediate the handle angles shown in FIGS. 2 and 5A. Other handle configurations, including those disclosed in U.S. Pat. No. 5,498,256 to Furnish et al. and U.S. Pat. No. 8,512,315 to Leonard et al. (each of which is incorporated herein by reference), often did not include a removable tool body, nor provide for an ability to readily and interchangeably use tool bodies with other handle configurations.

Currently, tool bodies are generally configured for use with just one of the handle configurations noted, and many devices are unitary, without even having the ability to exchange tool bodies between identical handles. It will be particularly useful to provide a linkage system for a handle that will provide for using the same tool bodies interchangeably between the different handle configurations. This will present advantages in the operating room for efficiency and effectiveness of surgical personnel, as well as potentially reducing procedure time and equipment costs, both of which are valuable areas for innovation.

Figure 2D:
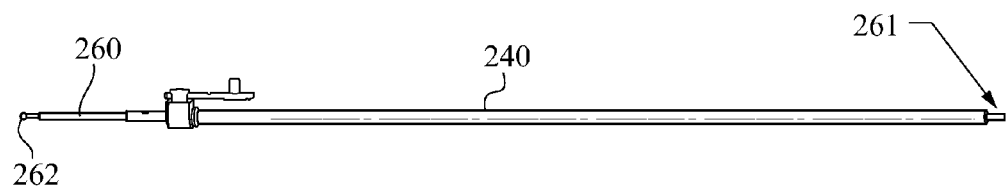
FIG. 2D shows an assembled tool body of FIG. 2.

The present disclosure includes a linkage system that provides for easily-releasable engagement (e.g., using the two-button system described above for quick, single-touch release) of a single tool body to any of the handles shown in FIGS. 2, 5A, and 5B. An assembled tool body including an outer shaft 240 and an inner rod 260 is shown in FIG. 2D, without a tool tip installed at the distal end (in contrast with the disassembled view of FIG. 2, which includes an installed tool tip 270 on the rod 260).

Figure 6:
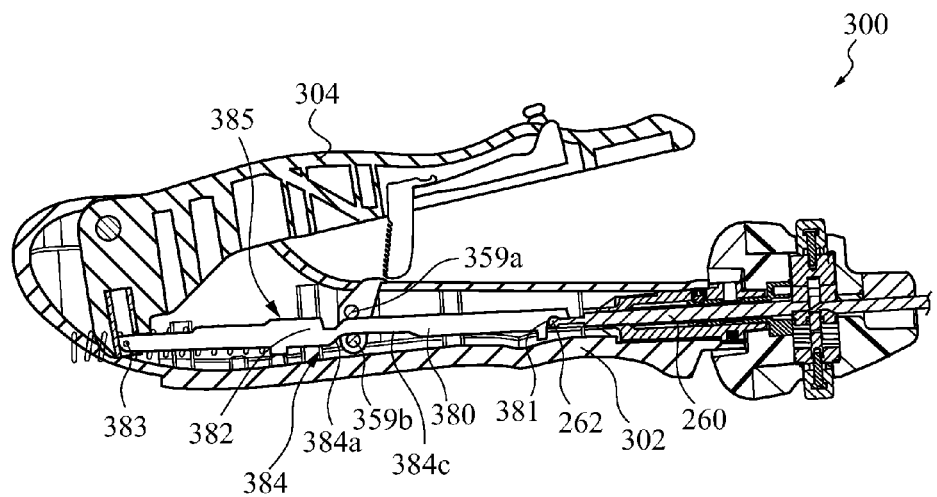
FIGS. 6-6A show a handle configured in the manner of the FIG. 5A embodiment, with a second handle member shown, respectively, in an actuation-range position and in an over-rotated (tool-body engagement/disengagement) position.
Figure 6A:
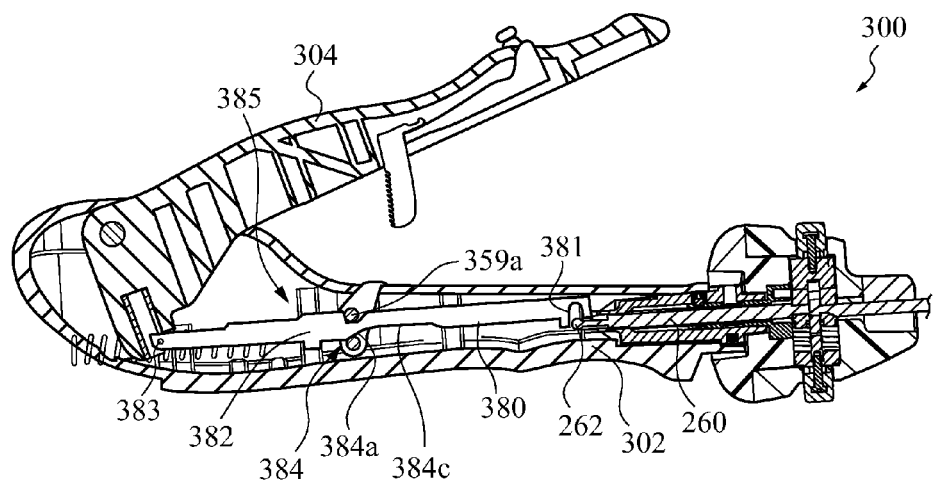
Figure 6B:
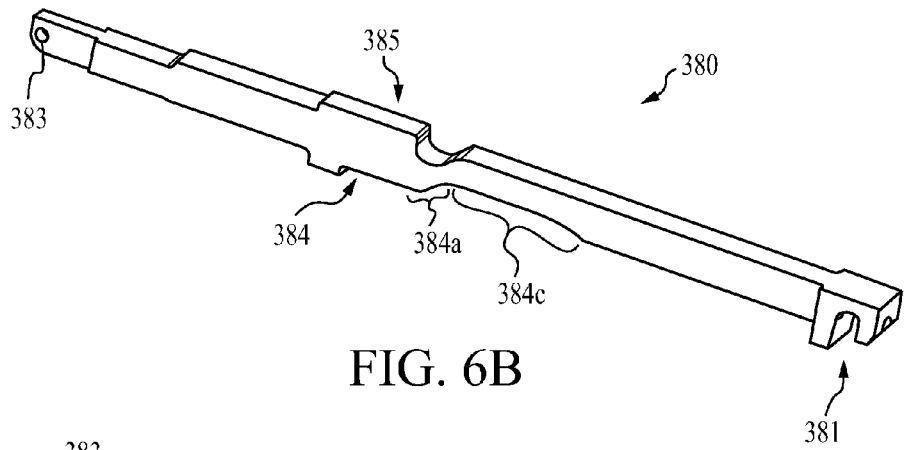
FIGS. 6B-6C show perspective views of a linkage member embodiment for the handle of FIGS. 6-6A.
Figure 6C:
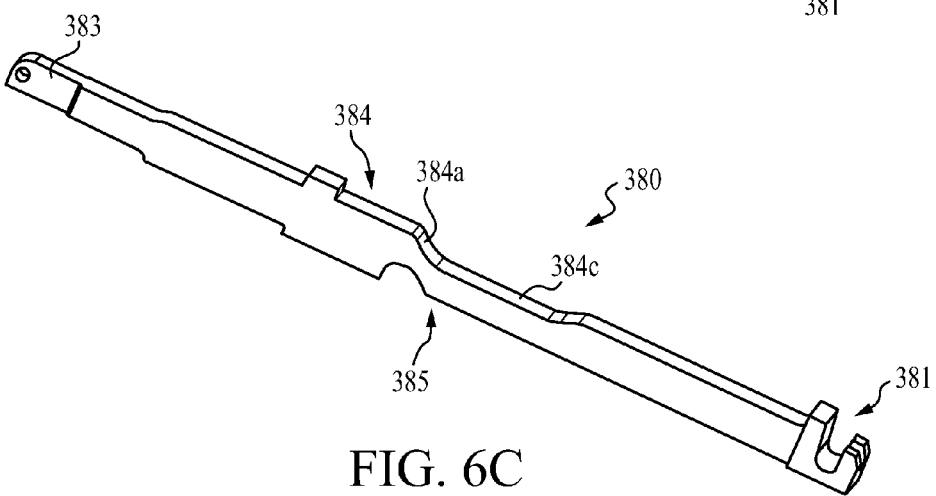

A first embodiment of a linkage member 380 is shown in FIGS. 6B-6E, for use in and with an in-line handle 300 shown in longitudinal section view (with a truncated tool body view) in FIGS. 6-6A. This handle configuration corresponds to that shown in FIG. 5A. The linkage member 380 includes an elongate body with a distal-end ball-engagement cage 381, an intermediate dual-camming region 382, and a proximal-end pivotable attachment structure 383. A first side 384 of the intermediate dual-camming region 382 includes a first contact portion 384a that is offset from, and oriented along a different (non-collinear) plane than, a generally longitudinal second contact portion 384c (where the planes of the first and second contact portions may be generally curved or flat).

Figure 6D:
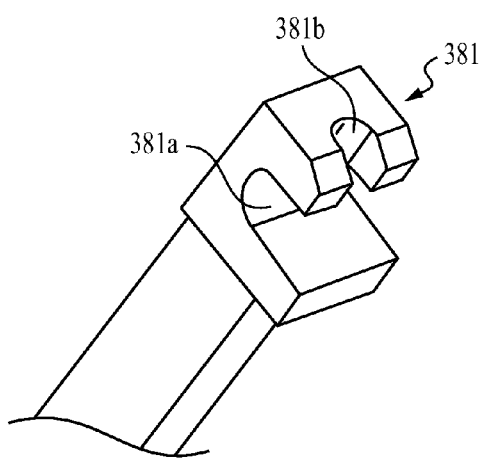
FIGS. 6D-6E show detail perspective views of a ball cage for a linkage member embodiment of FIGS. 6B-6C.
Figure 6E:
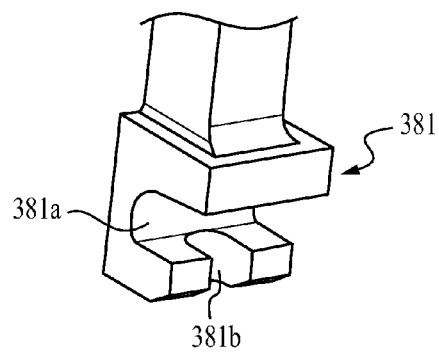

As shown in greater detail in FIGS. 6D-6E, the ball cage 381 includes a ball-receiving socket 381a configured to snugly and securely receive a ball 262 of a tool body inner rod 260. The partially-closed distal end of the ball-receiving socket 381a also includes a notch 381b configured to engage circumferentially around at least a portion of the inner rod 260 immediately adjacent the ball 262 where the rod diameter is less than the ball diameter. As will be understood with reference to FIGS. 6-6A and to FIGS. 6D-6E, the orientation of the ball cage 381 and its socket 381a and notch 381b are dimensioned, oriented, and located to receive a ball 262 when a tool body including an inner rod 260 is being installed with a handle 300 including the linkage member 380.

FIG. 6 shows the handle 300 with the ball cage 381 engaged around the ball 262. When the handle 304 is actuated within normal actuation parameters, the second contact surface 384c of the linkage member 380 rides along the camming surface of the lower pin 359b. Reciprocating (up/down) actuation of the second handle member 304 corresponds to movement of the linkage along a line that is generally congruent with or parallel to a central longitudinal axis of the first handle and, perhaps more relevant, along the central longitudinal axis of the inner actuation rod 260 such that it moves reciprocatingly to actuate a tool tip.

As shown in FIG. 6A, the second handle member 304 (attached to the proximal end 383 of the linkage member 380) may be over-rotated away from the first handle member 306 to push the linkage member distally. This lifts the ball cage 381 out of a longitudinal axis defined by the inner rod 260 so that the ball 262 can be moved into or out of an engagement position relative to the ball cage 381. This out-of-axis movement is effected in part by interaction of first and second camming surfaces provided, respectively, by upper and lower pins 359a, 359b. In this embodiment, these pins are collinear with mounting screws for a ratchet pawl member 248. When the second handle member 304 is over-rotated, the first contact portion 384a contacts the lower pin 359a. Specifically, distal movement of the linkage member relative to the pins 359a, 359b levers the distal ball cage 381 upward, and proximal movement of the linkage member relative to the pins 359a, 359b levers the distal ball cage 381 downward (e.g., to where it will engage around an appropriately disposed ball 262).

As shown in FIG. 6, when the rod 262 is fully installed to this handle embodiment 300, the ball cage 381 fully and securely engages around a significant portion of the ball such that handle actuation (of the second handle member 304) predictably transmits force to and through the inner rod 260 so as to move it reciprocatingly relative to the outer shaft, along its longitudinal axis. During this generally longitudinal linear reciprocation, the second contact portion 384c of the linkage member 380 rides along or adjacent the lower pin 359b and generally linearly between the upper and lower pins 359a, 359b. A second side 385 of the intermediate dual-camming region 382 is opposite the first side 384 and is configured to interact complementarily with the upper pin 359a to facilitate the structure and function described above.

Figure 7:
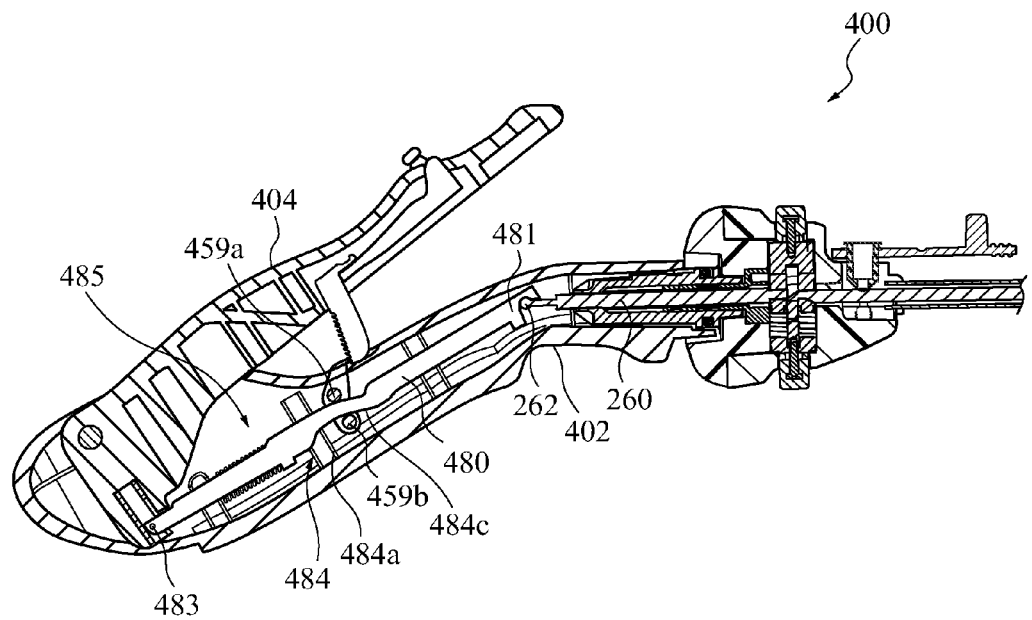
FIGS. 7-7A show a handle configured in the manner of the FIG. 5B embodiment, with a second handle member shown, respectively, in an actuation-range position and in an over-rotated (tool-body engagement/disengagement) position.
Figure 7A:
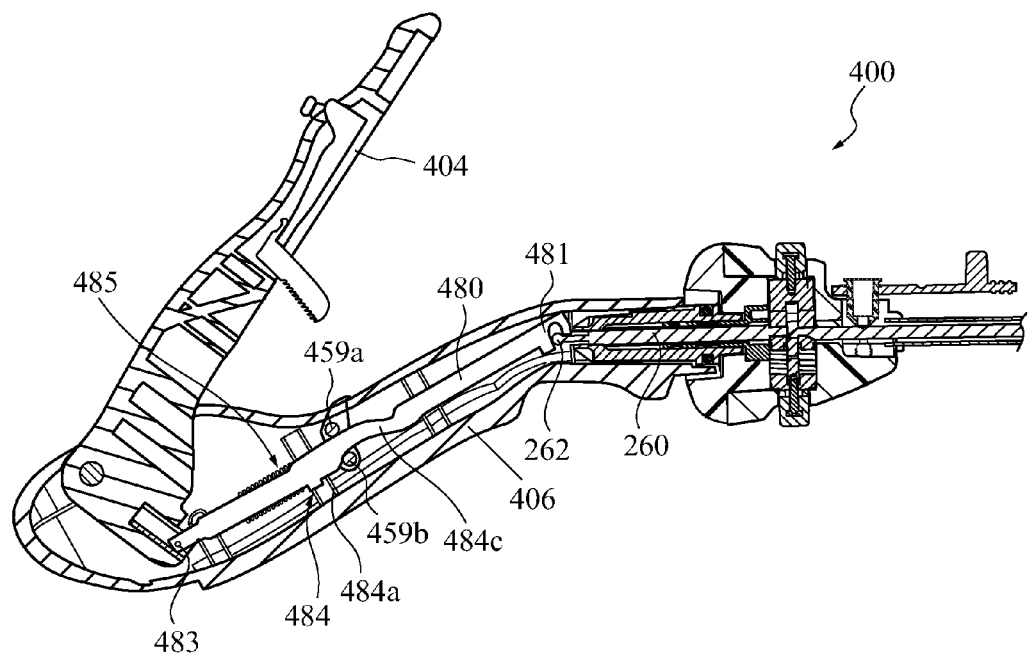
Figure 7B:
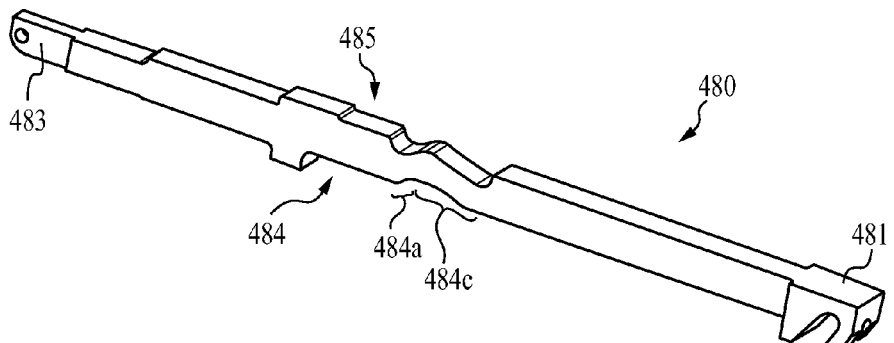
FIGS. 7B-7C show perspective views of a linkage member embodiment for the handle of FIGS. 7-7A.
Figure 7C:
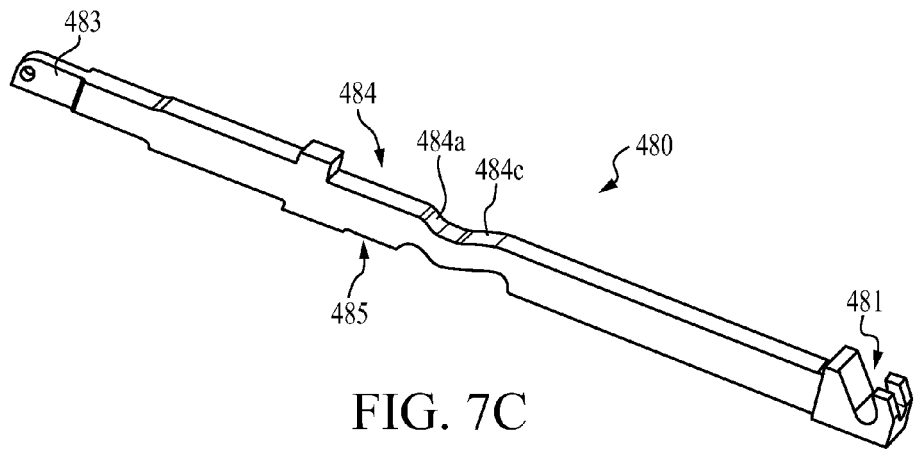

A second embodiment of a linkage member 480 is shown in FIGS. 7B-7E, for use in and with an offset-pistol-grip handle 400 shown in longitudinal section view (with a truncated tool body view) in FIGS. 7-7A. This handle configuration corresponds to that shown in FIG. 5B. The linkage member 480 includes an elongate body with a distal-end ball-engagement cage 481, an intermediate dual-camming region 482, and a proximal-end pivotable attachment structure 483. A first side 484 of the intermediate dual-camming region 482 includes a first contact portion 484a that is offset from, and oriented along a different (non-collinear) plane than, a generally longitudinal second contact portion 484c (where the planes of the first and second contact portions, whether curved or flat, may be generally parallel).

Figure 7D:
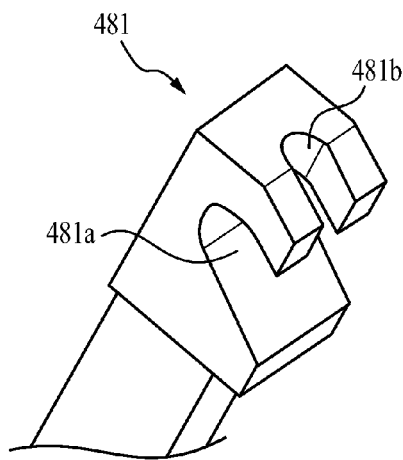
FIGS. 7D-7E show detail perspective views of a ball cage for a linkage member embodiment of FIGS. 7B-7C.
Figure 7E:
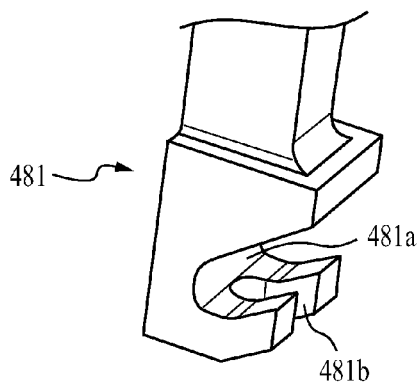

As shown in greater detail in FIGS. 7D-7E, the ball cage 481 includes a ball-receiving socket 481*a* configured to snugly and securely receive a ball 262 of a tool body inner rod 260, and also includes a notch 481*b* configured to engage circumferentially around at least a portion of the inner rod 260 immediately adjacent the ball 262. As will be understood with reference to FIGS. 7-7A and to FIGS. 7D-7E, the orientation of the ball cage 481 and its socket 481*a* and notch 481*b* are dimensioned, oriented, and located to receive a ball 262 when a tool body including an inner rod 260 is being installed with a handle 300 including the linkage member 480.

As shown in FIG. 7A, the second handle member 404 (attached to the proximal end 483 of the linkage member 480) may be over-rotated away from the first handle member 406 to push the linkage member distally. This lifts the ball cage 481 out of a longitudinal axis defined by the inner rod 260 so that the ball 262 can be moved into or out of an engagement position relative to the ball cage 481. This out-of-axis movement is effected in part by interaction of first and second camming surfaces provided, respectively, by upper and lower pins 459*a*, 459*b*. In this embodiment, these pins are collinear with mounting screws for a ratchet pawl member 248. When the second handle member 404 is over-rotated, the first contact portion 484*a* contacts the lower pin 459*a*. Specifically, distal movement of the linkage member relative to the pins 459*a*, 459*b* and contact with the first contact portion 484*a* levers the distal ball cage 481 upward, and proximal movement of the linkage member relative to the pins 459*a*, 459*b* levers the distal ball cage 481 downward (e.g., to where it will engage around an appropriately disposed ball 262).

As shown in FIG. 7, when the rod is fully installed, the ball cage 481 fully and securely engages around a significant portion of the ball such that handle actuation (of the second handle member 404) predictably transmits force to and through the inner rod 260 so as to move it reciprocatingly relative to the outer shaft, along its longitudinal axis. During this generally longitudinal linear reciprocation, the second contact portion 484*c* of the linkage member 480 rides along or adjacent the lower pin 459*b* and generally linearly between the upper and lower pins 459*a*, 459*b*. A second side 485 of the intermediate dual-camming region 482 is opposite the first side 484 and is configured to interact complementarily with the upper pin 459*a* to facilitate the structure and function described above.

Figure 8:
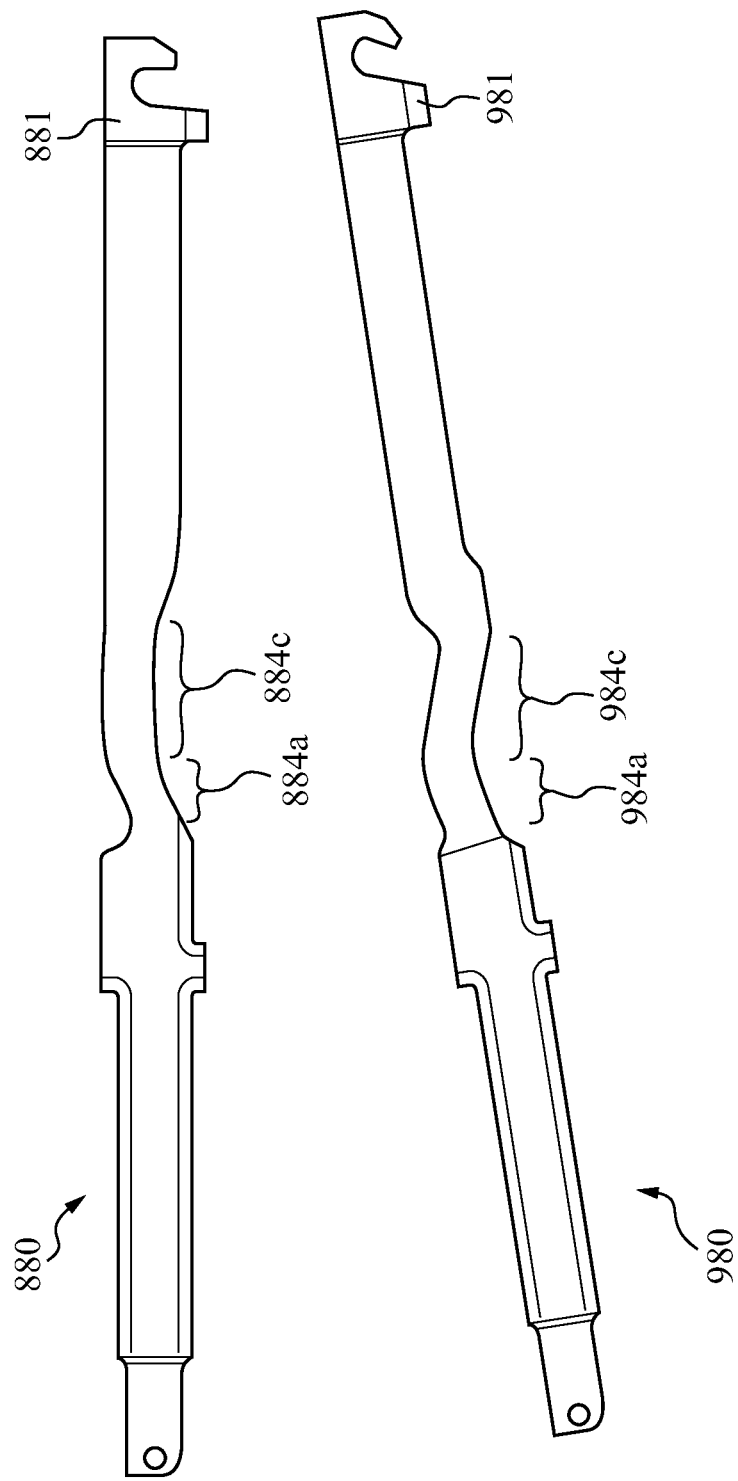
FIG. 8 shows, in parallel, side views of linkage member embodiments for an in-line handle and an off-set pistol grip handle.

FIGS. 6-6A and 7-7A, and the functionality of the linkage members 380, 480 may be further understood with reference to FIG. 8, which shows them aligned relative to each other in the position/alignment where each is shown in, respectively, FIG. 6 and FIG. 7. References to other handle components not shown in FIG. 8 (e.g. lower pin 359*b*, ball 262 of rod 260, etc.) should be understood with reference to FIG. 6 for the in-line embodiment and to FIG. 7 for the off-set pistol-grip embodiment.

A horizontal linkage embodiment 880 is (like linkage member 380 from FIGS. 6-6A) configured for use in an in-line handle. The horizontal linkage embodiment is shown in the upper portion of FIG. 8, with the first contact surface 884*a* that will, when advanced distally (left to right in the image), contact the lower pin 359*b* and will angle up the distal ball cage 881 out of its current long axis to disengage from a ball 262. The line followed for that motion intersects with the line that will be followed when the second contact surface 884*c* rides back and forth (right/left) across the lower pin 359*b* in a manner providing for generally longitudinal reciprocation of an actuation rod relative to a handle body and outer shaft. Those of skill in the art of mechanical design will appreciate, in view of the present disclosure, that the lines of motion (and the contact surfaces that define them) may be straight or may have some curvature.

Similarly, but with modification for use in and oriented to show congruence with the offset angle of the off-set pistol-grip handle 400 shown in FIG. 7 (an angle shown here as about 30°), an angled linkage member embodiment 880 is shown in the lower portion of FIG. 8. Its first contact surface 984*a* will, when advanced distally (generally left to right in the image), contact the lower pin 459*b* and will angle up the distal ball cage 981 out of its current long axis to disengage from a ball 262. The line followed for that motion intersects with the line that will be followed when the second contact surface 984*c* rides back and forth (right/left) across the lower pin 459*b* in a manner providing for generally longitudinal reciprocation of an actuation rod relative to a handle body and outer shaft. The shape and relative orientation of the ball cage 981 and contact surfaces 984*a*, 984*c* differ from the horizontal embodiment in a manner providing the functionality described above.

As such, each of the linkage embodiments includes an engagement/disengagement region x84a along a first line, and an actuation region x84c along a second line. For each of these and the above-described embodiments, actuation of the handle that effects movement/contact along the actuation line/region will most preferably correspond to standard operating tolerances for opening/closing or otherwise actuating a tool tip of the surgical device. Over-rotation of the handle that moves the engagement/disengagement region into contact with internal handle components (e.g., pins 359/459) will slide and/or lever the distal ball cage into or out of a position for engaging a ball 262 of an actuation rod 260 of a tool body. It should be appreciated that the outer contours of ball cage surfaces and other surfaces of linkage member embodiments may be squared, rounded, or otherwise configured in a manner to fit and operate within a handle cavity without affecting the first and second lines defined by the first and second contact surfaces. Also, the socket of each ball cage may be tooled, molded, or otherwise worked/configured to form a generally spherical cavity that will conform around a proximal-end ball of an actuation rod.

In one aspect, certain embodiments may include a system or kit that includes more than one handle configuration (e.g., two or more of the handle configurations shown in FIGS. 2A, 5A, and 5B and/or other handle configurations). Such a system or kit may also include a plurality of tool bodies including an outer rod an inner shaft as described above. For embodiments where a tool tip is affixed onto an inner rod (constructed in a manner such as other tool/rod assemblies known in the art including the V. Mueller Switchblade® type of products), a plurality of such "rod+tip" configurations with different procedure-appropriate tool tips (e.g., biopsy forceps, straight or curved cutting scissors, graspers, clamps, retractors, and/or other tool tips known in the art) may be provided, where the handle configurations are interchangeable between engagement with the different tool bodies without special adapters or other modification. For embodiments with a removable tool tip, a plurality of such tool tips may be provided as part of the system or kit. As such, a system of the present disclosure can provide two or more different handle configurations with two or more readily-interchangeable tool bodies (each of which may have a plurality of tool tips for different surgical tasks). This ability for ready interchange of parts provides unique advantages for the present system as compared to previous systems.

Those of skill in the art will appreciate that there are known means for controlling the relative position/bias of the ratchet members disclosed above that are appropriate for use within the scope of the present invention, and that different materials may be useful in embodiments of the present invention, and particular ratchet systems (including, for example, those described in U.S. Pat. No. 7,846,177 to Carpenter et al. and U.S. Pat. No. 8,512,315 to Leonard et al., and U.S. Pat. App. Publ. No. 2010/0191225 to Leonard et al., each of which is incorporated by reference). Those of skill in the art will appreciate that embodiments not expressly illustrated herein may be practiced within the scope of the present invention, including that features described herein for different embodiments may be combined with each other and/or with currently-known or future-developed technologies while remaining within the scope of the claims presented here. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment of the invention.

We claim:

1. A surgical instrument, comprising:
   a handle comprising:
     a first handle member;
     a second handle member including a second handle member proximal end portion pivotably attached to a proximal end portion of the first handle member; and
   an actuation mechanism configured to provide a releasable connection between the handle and a tool body, the actuation mechanism comprising an elongate linkage member disposed longitudinally within the first handle member,
     where the linkage member includes an elongate body with a distal-end ball-engagement cage, an intermediate dual-camming region, and a proximal-end pivotable attachment structure that is attached to the second handle member,
     where a first side of the intermediate dual-camming region slidably contacts a first camming surface within the first handle member, said first side including a generally longitudinal first contact portion and a second generally longitudinal contact portion offset from the first contact portion,
     where the first side of the intermediate dual-camming region is dimensioned such that generally longitudinal movement of the linkage member along and relative to the first camming surface occurs along a first line when the first contact portion contacts the first camming surface and occurs along a second line, non-collinear with the first line, when the second contact portion contacts the first camming surface.

2. The surgical instrument of claim 1, further comprising a tool body, the tool body comprising:
   a tubular outer shaft removably attached to the first handle member;
   an inner rod extending through a longitudinal lumen of the outer shaft and including a proximal engagement ball, said proximal engagement ball having a larger outer diameter than the diameter of a longitudinal inner rod portion extending through the outer shaft, where the ball is removably receivingly engaged by the ball cage and thereby mechanically communicates with the second handle member in a manner providing reciprocal longitudinal movement relative to the outer shaft.

3. The surgical instrument of claim 2, wherein one of the handle and the tool body further comprises an indexing knob configured to rotate the tool body, relative to the handle, about a central longitudinal axis of the tool body.

4. The surgical instrument of claim 2, where the second line is generally congruent with or parallel to a central longitudinal axis of the first handle, and the second line is at an intersecting angle relative to the first line,
   where the lines are oriented such, and the first camming surface, an intermediate transition surface of the linkage member, and a second camming surface are oriented such, that proximal-ward movement of the intermediate transition surface across the second camming surface moves the ball cage into engagement around the proximal engagement ball of the tool body.

5. The surgical instrument of claim 2, further comprising a tool tip attached to a distal portion of the outer shaft and the inner rod.

6. The surgical instrument of claim 1, where the handle is configured as one of an in-line grip handle or an offset pistol-grip handle.

7. The surgical instrument of claim 2, wherein the linkage member provides for interchangeable mounting of the tool body, which tool body is configured particularly for direct mounting into a selected pistol-grip handle, into any of:
   said handle configured as an in-line grip handle, and
   said handle configured as an offset pistol grip handle.

8. The surgical instrument of claim 2, where movement along the first line directs the ball cage, engaged around the ball, along an axis that is collinear with or parallel to a longitudinal axis defined by the inner rod.

9. The surgical instrument of claim 2, where distal movement of the linkage member along the second line directs the ball cage out of engagement around the ball, or proximal movement of the linkage member along the first line directs the ball cage into engagement with the ball.

10. The surgical instrument of claim 1, further comprising a ratchet mechanism for engaging the first handle member and second handle member.

11. The surgical instrument of claim 1, where at least one of the first camming surface and a second camming surface remains in contact with a surface of the linkage member throughout an operation of the handle.

12. A surgical instrument system comprising:
   a surgical instrument according to claim 1, where the handle is a first handle;
   a first tool body comprising:
     a tubular outer shaft removably attached to the first handle member;
     an inner rod extending through a longitudinal lumen of the outer shaft and including a proximal engagement ball, said proximal engagement ball having a larger outer diameter than the diameter of a longitudinal inner rod portion extending through the outer shaft, where the ball is removably receivingly engaged by the ball cage and thereby mechanically communicates with the second handle member in a manner providing reciprocal longitudinal movement relative to the outer shaft; and
   at least one tool tip removably engageable with a distal end of the first tool body.

13. The surgical instrument system of claim 12, where the at least one tool tip comprises a plurality of interchangeable tool tips.

14. The surgical instrument system of claim 12, further comprising a second tool body.

15. The surgical instrument system of claim 12, further comprising at least one second handle configured differently from the first handle, where the at least one second handle is selected from a pistol-grip handle, an in-line grip handle, and an offset pistol-grip handle.

16. A surgical instrument system comprising:
a surgical instrument according to claim 1, where the handle is a first handle;
a first tool body comprising:
a tubular outer shaft removably attached to the first handle member;
at least one inner rod extending through a longitudinal lumen of the outer shaft and including a proximal engagement ball, said proximal engagement ball having a larger outer diameter than the diameter of a longitudinal inner rod portion extending through the outer shaft, where the ball is removably receivingly engaged by the ball cage and thereby mechanically communicates with the second handle member in a manner providing reciprocal longitudinal movement relative to the outer shaft; and
at least one tool tip affixed to a distal end of the at least one inner rod and removably engageable with a distal end of the tubular outer shaft.

17. The surgical instrument system of claim 16, where the at least one tool tip comprises a plurality of tool tips, each affixed to an inner rod and forming thereby an interchangeable unit removably engageable from the handle and outer rod.

18. The surgical instrument system of claim 16, further comprising at least one second handle configured differently from the first handle, where the at least one second handle is selected from a pistol-grip handle, an in-line grip handle, and an offset pistol-grip handle.

19. A surgical instrument handle comprising:
a first handle member;
a second handle member including a second handle member proximal end portion pivotably attached to a proximal end portion of the first handle member; and
an actuation mechanism configured to provide a releasable connection between the handle and a tool body, the actuation mechanism comprising an elongate linkage member disposed longitudinally within the first handle member,
where the linkage member includes an elongate body with
a distal-end ball-engagement cage,
an intermediate dual-camming region, and
a proximal-end pivotable attachment structure that is attached to the second handle member and that provides for generally longitudinal reciprocating movement of the linkage member when the second handle member is pivoted relative to the first handle member,
where a first side of the intermediate dual-camming region slidably contacts a first camming surface within the first handle member, said first side including a generally longitudinal first contact portion and a second generally longitudinal contact portion offset from the first contact portion,
where the first side of the intermediate dual-camming region is dimensioned such that generally longitudinal movement of the linkage member along and relative to the first camming surface occurs along a first line when the first contact portion contacts the first camming surface and occurs along a second line, non-collinear with the first line, when the second contact portion contacts the first camming surface.

20. The surgical instrument handle of claim 19, further comprising a tool body including a proximal-end ball received by the ball cage.

* * * * *